(12) United States Patent
Wen et al.

(10) Patent No.: US 9,833,543 B2
(45) Date of Patent: Dec. 5, 2017

(54) IMPLANTABLE SCAFFOLDS AND METHODS OF USE

(71) Applicants: Jie Wen, St. Johns, FL (US); Nell Herrera Wirth, Roseville, MN (US); Patrick E Guire, Hopkins, MN (US)

(72) Inventors: Jie Wen, St. Johns, FL (US); Nell Herrera Wirth, Roseville, MN (US); Patrick E Guire, Hopkins, MN (US)

(73) Assignee: INNOVATIVE SURFACE TECHNOLOGIES, INC., St. Paul, MN (US)

( * ) Notice: Subject to any disclaimer, the term of this patent is extended or adjusted under 35 U.S.C. 154(b) by 569 days.

(21) Appl. No.: 14/351,145

(22) PCT Filed: Oct. 11, 2012

(86) PCT No.: PCT/US2012/059709
§ 371 (c)(1),
(2) Date: Apr. 11, 2014

(87) PCT Pub. No.: WO2013/055889
PCT Pub. Date: Apr. 18, 2013

(65) Prior Publication Data
US 2014/0294783 A1    Oct. 2, 2014

Related U.S. Application Data

(60) Provisional application No. 61/547,036, filed on Oct. 14, 2011.

(51) Int. Cl.
| | | |
|---|---|---|
| *A61L 27/56* | (2006.01) | |
| *A61L 27/18* | (2006.01) | |
| *A61K 9/00* | (2006.01) | |
| *A61L 27/22* | (2006.01) | |
| *A61L 27/38* | (2006.01) | |
| *A61L 27/54* | (2006.01) | |
| *A61L 27/58* | (2006.01) | |
| *A61K 38/00* | (2006.01) | |

(52) U.S. Cl.
CPC ............ *A61L 27/18* (2013.01); *A61K 9/0024* (2013.01); *A61L 27/22* (2013.01); *A61L 27/3847* (2013.01); *A61L 27/54* (2013.01); *A61L 27/56* (2013.01); *A61L 27/58* (2013.01); *A61K 38/00* (2013.01); *A61L 2400/12* (2013.01); *A61L 2430/02* (2013.01)

(58) Field of Classification Search
None
See application file for complete search history.

(56) References Cited

U.S. PATENT DOCUMENTS

| | | |
|---|---|---|
| 5,866,155 A | 2/1999 | Laurencin et al. |
| 7,291,345 B2 | 11/2007 | Winterbottom et al. |
| 7,731,756 B2 | 6/2010 | Maspero et al. |
| 7,772,393 B2 | 8/2010 | Guire et al. |
| 7,989,619 B2 | 8/2011 | Guire et al. |
| 8,487,137 B2 | 7/2013 | Guire et al. |
| 2008/0175885 A1 | 7/2008 | Asgari |
| 2009/0234459 A1 | 9/2009 | Sporring et al. |
| 2010/0292791 A1* | 11/2010 | Lu .......................... A61K 38/18 623/13.12 |
| 2011/0020917 A1 | 1/2011 | Wen et al. |
| 2011/0066242 A1 | 3/2011 | Lu et al. |
| 2013/0303759 A1 | 11/2013 | Guire et al. |

FOREIGN PATENT DOCUMENTS

WO   WO 2009/002869   * 12/2008

OTHER PUBLICATIONS

Yoshimoto et al. "A biodegradable nanofiber scaffold by electrospinning and its potential for bone tissue engineering" Biomaterials 24 (2003) 2077-2082.*
Lin et al. "Preparation of Macroporous Biodegradable PLGA Scaffolds for Cell Attachment with the Use of Mixed Salts as Porogen Additives" Journal of Biomedical Materials Research, vol. 63, Issue 3, Version of Record online: Mar. 15, 2002.*
Patricio et al. "Mechanical and Biological Behaviour of PCL and PCL/PLA Scaffolds for Tissue Engineering Applications" Chemical Engineering Transactions, 32, 1645-1650, 2013.*
Rodrigues et al. "Manufacture and Characterisation of Porous PLA Scaffolds" Procedia CIRP vol. 49, 2016, pp. 33-38.*
Yin et al. "Engineering Porous Poly(lactic acid) Scaffolds with High Mechanical Performance via a Solid State Extrusion/Porogen Leaching Approach" Polymers 2016, 8, 213, 13 pages.*
International Search Report for corresponding PCT/US2012/059709 (10 pages).
Wei, G. et al., Macroporous and Nanofibrous Polymer Scaffolds and Polymer/bone-Like Apatite Composite Scaffolds Generated by Sugar Spheres, J. Biomed. Mater. Res. 78A:306-315 (2006).
Dahlin, R. et al., Polymeric Nanofibers in Tissue Engineering, Tissue Engineering: Part B, 17(5):349-364 (2011).
Gomes, M.E., et al., Biodegradable polymers and composites in biomedical applications: from catgut to tissue engineering, Part 2 Systems for temporary replacement and advanced tissue regeneration, International Materials Reviews, 49(5):261-273 (2004).
Jiang, T., et al., In vitro evaluation of chitosan/poly(lactic acid-glycolic acid) sintered microsphere scaffolds for bone tissue engineering, Biomaterials 27:4894-4903 (2006).
Kofron, M., et al., Protein- and gene-based tissue engineering in bone repair, Current Opinion in Biotechnology 15:399-405 (2004).
Langer, R., Selected advances in drug delivery and tissue engineering, J. of Controlled Release 62:7-11 (1999).

(Continued)

*Primary Examiner* — Thane Underdahl
(74) *Attorney, Agent, or Firm* — Weaver Legal and Consulting LLC; Karrie Gemignani Weaver

(57) ABSTRACT

Inventive concepts relate general to the field of implantable three-dimensional scaffolds. More particularly, methods of preparing and using implantable nanofibrous tissue scaffolds are described. Inventive scaffolds can be used for treatment of defects in a living organism, such as hard or soft tissue defects including bone.

19 Claims, 3 Drawing Sheets

(56) References Cited

OTHER PUBLICATIONS

Liu, G., et al., Tissue-engineered bone formation using human bone marrow stromal cells and novel 3-tricalcium phosphate, Biomed. Mater. 2:78-86 (2007).
Ramakrishna, S., et al., Electrospun nanofibers: solving global issues, Materials Today 9(3):40-50 (2006).
Thomson, R.C., et al., Biodegradable Polymer Scaffolds to Regenerate Organs, Advances in Polymer Science 122:245-274 (1995).
Venugopal, J., et al., Biocomposite nanofibres and osteoblasts for bone tissue engineering, Nanotechnology 18:055101, 8 pages (2007).
Yu, M-F., New Process Makes Nanofibers in Complex Shapes and Unlimited Lengths, news@illinois.edu publication, 1 page (Jan. 30, 2008).
Licensing Technology Network, Process for Collecting and Spinning Nano-Fiber Yarns, published online by yet2.com, tow0039814. pdf (Oct. 28, 2007).

* cited by examiner

IMPLANTABLE SCAFFOLDS AND METHODS OF USE

CROSS REFERENCE TO RELATED APPLICATIONS

This application is a U.S. National Stage Application of International Application No. PCT/US2012/059709, entitled IMPLANTABLE SCAFFOLDS AND METHODS OF USE, filed on Oct. 11, 2012, which claims benefit under 35 U.S.C. §119(e) to U.S. Patent Application Ser. No. 61/547,036, entitled "IMPLANTABLE SCAFFOLDS AND METHODS OF USE," filed Oct. 14, 2011, the contents of which are incorporated herein in their entirety for all purposes.

GOVERNMENT FUNDING

This invention was made with government support under Grant Number 5R44EB005905, awarded by the National Institutes of Health (NIH), The government has certain rights in the invention.

FIELD OF THE INVENTION

Inventive concepts relate generally to the field of implantable three-dimensional scaffolds. Methods of preparing and using such implantable scaffolds are described. Inventive scaffolds can be used for treatment of defects in a living organism, such as hard or soft tissue defects including bone.

BACKGROUND

Generally speaking, tissue engineering involves a combination of living cells and a support structure called a scaffold. The scaffold, depending upon the tissue being produced, can be anything from a matrix of collagen, a structural protein, to a synthetic biodegradable polymer laced with chemical and biological cues that stimulate cell growth and multiplication. The cells initiating the process can come from laboratory cultures or from the patient's own body. The role of the scaffold (to induce surrounding tissue and cell ingrowth and/or to serve as matrices for transplanted cells to attach, grow and differentiate) is temporary, but important to the success of producing engineered tissues.

An ideal tissue engineering scaffold is biocompatible, biodegradable, porous, functionalizable and mechanically strong. Tissue scaffolds can be used to repair defects in hard tissues (such as bone) or soft tissues.

Bone grafting applications can be differentiated by the requirements of the skeletal site. Certain applications require a "structural graft" in which one role of the graft is to provide mechanical or structural support to the site. Such grafts should be fabricated of a material capable of providing the strength needed for load-bearing. The graft may also have beneficial biological properties, such as incorporation into the skeleton, osteoinduction, osteoconduction, and/or angiogenesis.

For areas of the body in which the mechanical load-bearing requirements of an implant can be challenging, lack of replacement by host bone tissue can compromise the implant by subjecting it to repeated load and cumulative unrepaired damage (mechanical fatigue) within the implant material. Thus, it is highly desirable that the implant have the capacity to support load initially, and be capable of gradually transferring this load to the host bone tissue as it remodels the implant.

SUMMARY OF THE INVENTION

Inventive concepts relate to methods of preparing implantable scaffolds composed of biodegradable, biocompatible polymer for use in treating defects in a living organism, such as tissue defects. The biodegradable, biocompatible polymer used to fabricate the scaffolds is synthetic. As discussed herein, "synthetic" refers to materials that are not naturally occurring. In this sense, synthetic polymers can comprise naturally-occurring polymers that have been modified in some manner (such as chemical modification) from their natural state. In some aspects, the synthetic polymers are not derived from tissues of vertebrate animals.

Thus, in some aspects, methods of producing a nanofibrous tissue scaffold are provided, such methods comprising steps of: (a) generating biodegradable, synthetic nanofibers; (b) processing the nanofibers to generate nanofibrous fragments; (c) compressing the nanofibrous fragments; and (d) heating the nanofibrous fragments to generate a porous nanofibrous tissue scaffold.

In accordance with inventive concepts, steps (c) and (d) can be performed simultaneously or sequentially. When performed sequentially, the particular order of sequence is not critical.

In some embodiments, the biodegradable, synthetic nanofibers include photoreactive moieties, and thus are photoreactive nanofibers. In some aspects, nanofibers can be generated by electrospinning. The synthetic nanofibers can, in some aspects, comprise polycaprolactone nanofibers. Optionally, one or more functional moieties (such as amine or acid groups) can be coupled to the synthetic nanofibers.

In some aspects, when the synthetic nanofibers comprise photoreactive nanofibers, inventive methods can further comprise a step of illuminating the photoreactive nanofibers. Such illumination can couple functional moieties or biomolecules to the photoreactive nanofibers and/or crosslink individual photoreactive nanofibers. Thus, in some aspects, methods of producing a nanofibrous tissue scaffold are provided, such methods comprising steps of: (a) generating biodegradable, synthetic photoreactive nanofibers; (b) processing the nanofibers to generate nanofibrous fragments; (c) compressing the nanofibrous fragments; (d) heating the nanofibrous fragments to generate a porous nanofibrous tissue scaffold; and (e) illuminating the photoreactive nanofibers. The particular order of steps (including sequential and/or simultaneous order) can be determined as desired.

Optionally, inventive methods can comprise a step of adding a void forming material (such as a salt, sugar or other crystalline material) to the nanofiber fragments prior to compression or heating. When such void-forming materials are included, inventive methods can optionally include a step of removing (such as by leaching) the material from the scaffold prior to use in a patient. Thus, in some aspects, methods of producing a nanofibrous tissue scaffold are provided, such methods comprising steps of: (a) generating biodegradable, synthetic nanofibers; (b) processing the nanofibers to generate nanofibrous fragments; (c) adding a void-forming material to the nanofibrous fragments; (d) compressing the nanofibrous fragments; (e) heating the nanofibrous fragments to generate a porous nanofibrous tissue scaffold; and (f) optionally removing the void-forming material from the nanofibrous tissue scaffold.

Optionally, inventive methods can include a step of coupling a biomolecule or bioactive agent to the synthetic nanofibers via the functional group. In some aspects, the biomolecule can comprise an osteogenic protein, such as, but not limited to, one or more bone morphogenic proteins (BMP) or one or more extracellular matrix (ECM) proteins. Thus, in some aspects, methods of producing a nanofibrous tissue scaffold are provided, such methods comprising steps of: (a) generating biodegradable, synthetic nanofibers; (b) processing the nanofibers to generate nanofibrous fragments; (c) compressing the nanofibrous fragments; (d) heating the nanofibrous fragments to generate a porous nanofibrous tissue scaffold; and (e) optionally coupling a biomolecule or bioactive agent to the nanofibrous tissue scaffold.

Also provided are three-dimensional nanofibrous scaffolds prepared from these methods useful in treatment of tissue defects, such as bone. In some aspects, the nanofibrous scaffold is an osteoimplant.

In some aspects, inventive tissue scaffolds can contain a unique combination of features that can overcome tissue regeneration issues, including one or more of the following: a porous nanoscaled surface texture for achieving favorable cell interactions, use of a well-known biocompatible and biodegradable polymer, and a photo-functionalizable surface for easy attachment of desired factors to fine tune the scaffold for optimal bone integration. Desirably, the porous nature of inventive nanofibrous scaffolds allows the scaffolds to exhibit a high surface-to-volume ratio to allow for cell attachment and ingrowth. In some aspects, inventive nanofibrous scaffold implants can provide one or more of the following advantages: can provide an osteoimplant possessing sufficient strength in a body fluid environment to enable the osteoimplant to bear loads; is porous to permit the osteoimplant to be revascularized and incorporated by the host; is osteogenic and thereby promotes new host bone tissue formation within and around the osteoimplant; provides a load-bearing osteoimplant that supports load initially and is capable of gradually transferring this load to the host bone tissue as it remodels the osteoimplant.

Mechanical loading plays a major role in the growth and development of bone tissues. Thus, when inventive nanofibrous scaffolds are utilized to repair bone tissues, it can be desirable for nanofibrous scaffold implants to have sufficient mechanical strength to withstand the hydrostatic pressures and to maintain the spaces required for cell in-growth and matrix production. In vivo, because bone is always under continuous stress, the mechanical properties of the implanted scaffold should ideally match (or closely approximate) those of living bone, so that an early mobilization of the injured site can be made possible. In addition to growth factors, it is known that mechanical forces stimulate the synthesis of extracellular proteins in vitro and in vivo and can affect the tissue's overall structure. For example, studies have shown that cartilage that is not mechanically stimulated will atrophy and that some stimulation is necessary to promote chondrogenesis. Generally speaking, the necessary mechanical properties are required to support bone growth, match those of living bones, and withstand mechanical stimulation during bone development.

Inventive scaffolds can be easily shaped into different forms, such as (but not limited to) blocks, cylinders, sheets and granules, for handling and use. The implant can be processed (for example, cut) into a shape of a wound site in a bone or can be shaped in a mold. The predetermined shape of the mold can be that of a wound site in a bone. Optionally, various biologically active substances, such as BMP, growth factors and ECM proteins can be bound to the nanofibrous scaffold network.

Inventive scaffolds can be used for various hard or soft tissue repair, including bone grafting and inpatient fracture repair.

DETAILED DESCRIPTION

Figure 1:
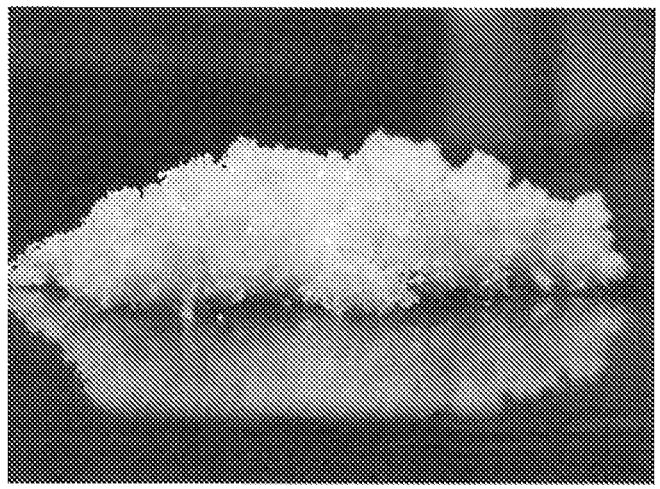
FIG. 1 illustrates nanofibrous fragments produced in accordance with inventive principles.

The embodiments of the present invention described herein are not intended to be exhaustive or to limit the invention to the precise forms disclosed. Rather, the embodiments are chosen and described so that others skilled in the art can appreciate and understand the principles and practices of the present invention. This application is intended to cover adaptations or variations of the present subject matter.

All publications and patents mentioned herein are hereby incorporated by reference to the same extent as if each individual publication or patent application was specifically and individually indicated by reference. The publications and patents disclosed herein are provided solely for their disclosure. Nothing herein is to be construed as an admission that any publication and/or patent is prior art.

In the specification and in the claims, the terms "including" and "comprising" are open-ended terms and should be interpreted to mean "including, but not limited to . . . ." These terms are broader than, and therefore encompass, the more restrictive terms "consisting essentially of" and "consisting of."

As used herein and in the appended claims, the singular forms "a," "an," and "the" include plural reference unless the context clearly dictates otherwise. As such, the terms "a" (or "an"), "one or more" and "at least one" can be used interchangeably herein.

Generally speaking, inventive concepts provide methods to prepare three-dimensional scaffolds having physical appearance and mechanical stability similar to trabecular (cancellous) bone. Methods use synthetic, biodegradable polymer nanofibers to create a porous structure. In some aspects, scaffolds prepared in accordance with inventive principles can be characterized by porosity in the range of about 30-40% porosity, and average pore size that is greater than 100 μm, or in the range of about 100 to about 300 μm. In some aspects, compressive modulus and compressive strength of the scaffolds can be comparable to trabecular bone; compressive modulus of inventive scaffolds can be in the range of about 50 to about 5000 MPa, or about 50 to about 4500 MPa, or about 50 to about 4000 MPa, or about 50 to about 2000 MPa. Compressive strength can be in the range of about 0.2 to about 10 MPa. By optimizing conditions of inventive methods described herein, one of skill in the art can readily prepare nanofibrous scaffolds having a wide variety of mechanical strength (compressive modulus and/or compressive strength) to match a selected tissue site to be repaired. Nanofibrous scaffolds in accordance with inventive concepts exhibit both micro-porous and nanofibrillar structures. Such micro-porous and nanofibrillar structures can, in some embodiments, provide an excellent environment for cellular ingrowth and proliferation.

As used herein, "osteoimplant" refers to implantable devices or materials that are intended for implantation at a bony site. This term is used in its broadest sense and is not intended to be limited to any particular shape, size, configuration or application. The term contemplates any device or material for implantation that aids or augments bone or other hard tissue formation or healing for human or animal use. Osteoimplants are often applied at a bone defect or dental repair site, for example, one resulting from injury, defect brought about during the course of surgery, infection, malignancy or developmental malformation. Given the diversity of uses, osteoimplants can be suitably sized and shaped as required for use in a wide variety of orthopedic, neurosurgical, oral and maxillofacial and dental surgical procedures such as the repair of simple and compound fractures and non-unions, external and internal fixations, joint reconstructions such as arthrodesis, general arthroplasty, deficit filling, discectomy, laminectomy, anterior cervical and thoracic operations, spinal fusions, dental restorations, and the like.

As used herein, "biomolecules" refers to classes of molecules (such as proteins, amino acids, peptides, polynucleotides, nucleotides, carbohydrates, steroids, and the like) that are commonly found in cells and tissues, whether the molecules themselves are naturally-occurring or artificially created (for example, by synthetic or recombinant methods). For example, biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA and RNA.

"Biocompatible" as used herein is intended to describe materials that, upon administration in vivo, integrate with the host tissue and do not induce undesirable long term effects in a patient's body (for example, do not elicit a significant, undesirable immune response). The term shall be understood to mean the absence of stimulation of an unacceptable biological response to an implant as distinguished from the sort of mild, transient inflammation and/or granulation response that may accompany implantation of foreign objects into a living organism and that is associated with the normal healing response.

"Biodegradable" materials are materials that degrade under physiological conditions to form a product that can be metabolized or excreted without damage to organs. Biodegradable materials are not necessarily hydrolytically degradable and may require enzymatic action to fully degrade. Biodegradable materials also include materials that are broken down within cells.

"Osteogenic" shall be understood as referring to the ability of an osteoimplant to enhance or accelerate the growth of new bone tissue by one or more mechanisms such as osteogenesis, osteoconduction and/or osteoinduction.

"Osteoinductive" is used to refer to the ability of a substance to recruit cells from the host that have the potential for forming new bone and repairing bone tissue. Most osteoinductive materials can stimulate the formation of ectopic bone in soft tissue.

"Osteoconductive" is used to refer to the ability of a non-osteoinductive substance to serve as a suitable template or substrate along which bone may grow.

"Implantable device" refers to any object implantable through surgical or other suitable means into a patient, whose primary function is achieved either through its physical presence or mechanical properties.

The term "incorporation" refers to the biological mechanisms whereby host cells gradually remove portions of the osteoimplant and replace the removed portions with native host bone tissue while maintaining strength. This phenomenon is also referred to in the scientific literature as "creeping substitution," "wound healing response," and "cellular based remodeling." As used herein, the term "incorporation" shall be understood as embracing what is considered by those skilled in the art to be conveyed by the aforementioned expressions.

The expression "wet compressive strength" as utilized herein refers to the compressive strength of the osteoimplant after the osteoimplant has been immersed in physiological saline (water containing 0.8 g NaCl/100 ml water) for a minimum of 12 hours and a maximum of 24 hours. Compressive strength is a well-known measurement of mechanical strength and is measured using the procedure described herein.

"Bioactive agents" is used to refer to compounds or entities that alter, inhibit, activate, or otherwise affect biological or chemical events. For example, bioactive agents can include, but are not limited to, anti-AIDS substances, anti-cancer substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, and imaging agents. In some embodiments, a bioactive agent can comprise a drug.

In accordance with inventive principles, biodegradable, synthetic polymer nanofibers are fabricated and processed to produce nanofibrous tissue scaffolds.

Suitable synthetic biodegradable polymers include, but are not limited to, aliphatic polyesters, polyols, and polycarbonates. Illustrative aliphatic polyesters include, but are not limited to, gylcol and dicarbonic acid polycondensates (such as poly(ethylene succinate) and poly(butylene terephthalate)); polylactides (such as polyglycolide and polylactides); polylactones (such as polycaprolactone); and poly(butylene terephthalate). Illustrative polyols include, but are not limited to, poly(vinyl alcohol). Illustrative polycarbonates include, but are not limited to, poly(ester carbonate). Other illustrative synthetic, biodegradable polymers include polyanhydrides, poly($\alpha$-cyanoacrylates), polyphosphazenes, polyamides, and poly(orthoesters). Other biodegradable polymers that can be derived from non-vertebrate sources (and are thus "synthetic" in accordance with inventive concepts), can include polysaccharides from plant origins (such as cellulose, starch and alginate).

In some aspects, suitable polymers include biodegradable aliphatic polyesters. One such biodegradable aliphatic polyester is polycaprolactone, which has a low melting point of around 60° C. and a glass transition temperature of about −60° C. Polycaprolactone is a desirable polymer for use in accordance with inventive concepts, as the polymer is a material which easily absorbs water because of its hydrophilic carboxylate groups.

In accordance with inventive principles, nanofibers can be fabricated from one or more than one synthetic polymer. For example, nanofibers can be formed from a blend of different synthetic polymers.

In some aspects, the synthetic, biodegradable polymers are combined with one or more photoreactive groups, to form photoreactive nanofibers for use in the invention. In some aspects, the photoreactive group is provided by a photoreactive crosslinker. Photoreactive crosslinkers can serve one or more purposes in inventive methods. In some embodiments, photoreactive crosslinkers can serve to crosslink nanofibers of the nanofibrous scaffold. In these aspects, such crosslinking between the individual nanofibers can improve mechanical strength and stability of the nanofibrous scaffold product. In some embodiments, photoreactive crosslinkers can serve as attachment sites for functionalized moieties (for example, polymers such as polyacid groups, amine groups, and the like). These functionalized moieties can provide the ability to attach biomolecules and/or bioactive agents to the formed scaffold product.

Nanofibers can be fabricated to include one or more different photoreactive groups. Further, nanofibers can be fabricated that include different concentrations of photoreactive groups, as illustrated in Example 2 (wherein electrospinning of nanofibers having two different concentrations of photoreactive crosslinker were simultaneously electrospun, to produce a nanofiber mesh having nanofibers with different concentrations of crosslinker).

Generally speaking, photochemistry uses the action of light to excite electrons within molecules. These excited states are generally quite short-lived and terminate by one of three pathways. The excited state can emit a photon from either a singlet state (fluorescence) or a triplet state (phosphorescence), lose its energy via vibrations in the form of heat, or react chemically. Because the absorption of a photon highly excites a molecule, there is a much wider variety of reactions possible than standard thermochemical means. Photocrosslinking uses these reactions to link small molecules to other small molecules, large molecules to small molecules, and large molecules to each other (photocoupling of polymers), as well as large and small molecules to substrates or particles (photobonding to surfaces). During photocrosslinking, each increase in a molecule's weight is initiated by its own photochemical reaction and the coupling of radicals can result in the formation of crosslinks, especially in the solid state. The crosslinking is generally between pre-existing polymer chains and includes polycondensation, which is also referred to as step growth polymerization. Photocrosslinking can usually be classified into two types.

The first type is where crosslinks are formed by the direct reaction of an excited molecule. Representative reactions would be a photo 2+2 cycloaddition (or 4+4) and cis-trans isomerization of double bonds. Examples of this type are demonstrated by the cyclodimerization of cinnamic acid and derivatives, chalcones and stilbenes, anthracenes, maleimides and strained cycloalkenes. In another class of reactions, the triplet, $T_1$ excited state of carbonyl groups in ketones can result in either fragmentation (Norrish Type I reaction) or hydrogen abstraction (Norrish Type II reaction). Both of these photoreactions create two radicals which can then subsequently react with surrounding molecules. For example, aromatic ketones, such as benzophenone, readily undergo hydrogen abstraction reactions with any preformed polymer possessing C—H bonds. It should be understood that incorporation of two or more photoreactive moieties, such as a benzophenone, would provide a multifunctional crosslinking photoreactive group.

The second usual type of photocrosslinking is where crosslinks occur through the action of a photogenerated reactive species. Examples of the second type include the use of nitrenes that are formed from organic azides or carbenes.

Whether through direct excited state reaction or reactive intermediates, photolysis of photoreactive crosslinking groups can begin a process of bond formation throughout a system. In most cases the system will include synthetic polymer nanofibers (such as polycaprolactone nanofibers). The act of crosslinking can serve to crosslink individual nanofibers within the system, thereby increasing durability of the nanofiber mesh used to form inventive scaffolds. Bond formation can take place by many means within the various systems. In many cases, radicals are formed through photolysis. Radicals can form new bonds through radical-radical recombination, addition to unsaturated bonds, hydrogen abstraction and subsequent recombination or addition, further fragmentation, oxygen addition, or disproportionation, as well as possible electron transfer reactions.

In cases which generate carbenes and nitrenes, bonds would be formed typically by insertion, hydrogen abstraction to form radicals, rearrangements, and the like. The excited states of some dienes and other unsaturated compounds may directly react with relevant groups on a polymer chain, as when cinnamic acid forms a 2+2 photoadduct with polybutadiene or other polymer containing double bonds. The invention is not limited to these described mechanisms, and in fact, many mechanisms may be at work within on polymer-photoreactive crosslinking group system.

Suitable photochemical crosslinkers are described, for example, in commonly owned U.S. Pat. No. 7,772,393 (Guire et al., issued Aug. 10, 2010), and commonly owned U.S. Pat. No. 7,989,619 (Guire et al., issued Aug. 2, 2011). While any of the crosslinkers described in these two patents are useful in accordance with inventive principles, the following crosslinkers from U.S. Pat. No. 7,772,393 are mentioned:

In one embodiment, a suitable crosslinker for use in accordance with inventive concepts has the formula:

wherein L is a linking group. D is O, S, SO, $SO_2$, $NR^5$ or $CR^6R^7$. T is $(—CH_2—)_x$, $(—CH_2CH_2—O—)_x$, $(—CH_2CH_2CH_2—O—)_x$, $(—CH_2CH_2CH_2CH_2—O—)_x$ or forms a bond. $R^1$ is a hydrogen atom, an alkyl, alkyloxyalkyl, aryl, aryloxyalkyl or aryloxyaryl group. X is O, S, or $NR^8R^9$. P is a hydrogen atom or a protecting group, with the proviso that P is absent when X is $NR^8R^9$. $R^2$ is a hydrogen atom, an alkyl, alkyloxyalkyl, aryl, aryloxylalkyl or aryloxyaryl group. G is O, S, SO, $SO_2$, $NR^{10}$, $(CH_2)_t$—O— or C=O. $R^3$ and $R^4$ are each independently an alkyl, aryl, arylalkyl, heteroaryl, or a heteroarylalkyl group, or optionally, $R^3$ and $R^4$ can be tethered together via $(—CH_2—)_q$, $(—CH_2—)_rC=O(—CH_2—)_s$, $(—CH_2—)_rS(—CH_2—)_s$, $(—CH_2—)_rS=O(—CH_2—)_s$, $(—CH_2—)_rS(O)_2(—CH_2—)_s$, or $(—CH_2—)_rNR(—CH_2—)_s$. $R^5$ and $R^{10}$ are each independently a hydrogen atom or an alkyl, aryl, or arylalkyl group. $R^6$ and $R^7$ are each independently a hydrogen atom, an alkyl, aryl, arylalkyl, heteroaryl or heteroarylalkyl group. $R^8$ and $R^9$ are each independently a hydrogen atom, an alkyl, aryl, or arylalkyl group, R is a hydrogen atom, an alkyl group or an aryl group, q is an integer from 1 to about 7, r is an integer from 0 to about 3, s is an integer from 0 to about 3, m is an integer from 2 to about 10, t is an integer from 1 to about 10 and x is an integer from 1 to about 500.

In one aspect, L is a branched or unbranched alkyl chain having between about 2 and about 10 carbon atoms.

In another aspect, D is an oxygen atom (O).

In still another aspect, T is (—CH$_2$—)$_x$ or (—CH$_2$CH$_2$—O—)$_x$ and x is 1 or 2.

In still yet another aspect, R$^1$ is a hydrogen atom.

In yet another aspect, X is an oxygen atom, O, and P is a hydrogen atom.

In another aspect, R$^2$ is a hydrogen atom.

In still another aspect, G is an oxygen atom, O.

In still yet another aspect, R$^3$ and R$^4$ are each individually aryl groups, which can be further substituted, and m is 3.

In one particular aspect, L is

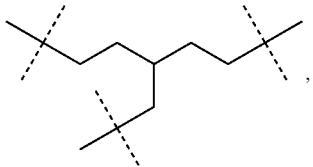

D is O, T is (—CH$_2$—)$_x$, R$^1$ is a hydrogen atom, X is O, P is a hydrogen atom, R$^2$ is a hydrogen atom, G is O, R$^3$ and R$^4$ are phenyl groups, m is 3 and x is 1.

In yet another particular aspect, L is (—CH$_2$—)$_y$, D is O, T is (—CH$_2$—)$_x$, R$^1$ is a hydrogen atom, X is O, P is a hydrogen atom, R$^2$ is a hydrogen atom, G is O, R$^3$ and R$^4$ are phenyl groups, m is 2, x is 1 and y is an integer from 2 to about 6, and in particular, y is 2, 4 or 6.

In certain embodiments, x is an integer from about 1 to about 500, more particularly from about 1 to about 400, from about 1 to about 250, from about 1 to about 200, from about 1 to about 150, from about 1 to about 100, from about 1 to about 50, from about 1 to about 25 or from about 1 to about 10.

In another embodiment, a suitable crosslinker for use in accordance with inventive concepts has the formula:

L-(T-C(R$^1$)(XP)CHR$^2$GR$^3$C(=O)R$^4$)$_m$ 

wherein L, T, R$^1$, X, P, R$^2$, G, R$^3$, R$^4$, R$^8$, R$^9$, R$^{10}$, R, q, r, s, m, t and x are as defined above.

In one aspect, L has a formula according to structure (I):

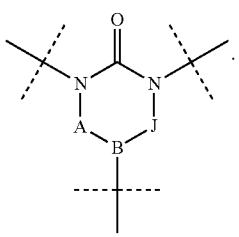

(I)

A and J are each independently a hydrogen atom, an alkyl group, an aryl group, or together with B form a cyclic ring, provided when A and J are each independently a hydrogen atom, an alkyl group, or an aryl group then B is not present, B is NR$^{11}$, O, or (—CH$_2$—)$_z$, provided when A, B and J form a ring, then A and J are (—CH$_2$—)$_z$ or C=O, R$^{11}$ is a hydrogen atom, an alkyl group, an aryl group or denotes a bond with T, each z independently is an integer from 0 to 3 and provided when either A or J is C=O, then B is NR$^{11}$, O, or (—CH$_2$—)$_z$ and z must be at least 1.

In another aspect T is —CH$_2$—.

One illustrative crosslinker, and a method of making the crosslinker, is described in Example 1.

The synthetic, biodegradable polymer can be combined with one or more crosslinking agents, and nanofibers can be subsequently formed from the combination. When crosslinker is combined with the synthetic, biodegradable polymer prior to nanofiber formation, such methods produce latent reactive nanofibers, which comprise synthetic, biodegradable polymer and one or more crosslinking agents. By incorporating photoreactive crosslinking groups into the nanofibers themselves, the photoreactive group loading is increased in individual nanofibers, and the photoreactive groups can be distributed throughout the structure of the nanofibers (as compared to simply being presented on the outer surface of the nanofibers).

Photoreactive nanofibers and methods of making them have been described, for example, in commonly owned U.S. Patent Application Publication No. 2011/0020917 (Wen, et al., published Jan. 27, 2011). While this patent publication describes broad discussion of latent reactive nanofibers and methods of producing them, the disclosure can be instructive for the synthetic, biodegradable nanofibers comprising photoreactive crosslinking agents in accordance with the present invention.

Optionally, inventive photoreactive nanofibers can be formulated to include one or more functional moieties. Such functional moieties can serve as attachment sites for desired components, such as biologically active molecules, non-bioactive molecules, and the like. In some embodiments, the functional moiety can comprise a functional polymer. Functional polymers are polymers that bear specified chemical groups (IUPAC Compendium of Chemical Terminology 2007). These specified chemical groups can be used for further chemical reactions. Illustrative functional moieties include, but are not limited to, carboxyl, amine, thiol, epoxy, n-hydroxysuccinimide (NHS), aldehyde, azide, phosphone, hydroxyl, or the like.

Generally speaking, a desired amount of nanofiber mesh is immersed in a solution of the functional moiety (for example, polyethyleneimine (PEI), polyacrylic acid (PAA) or a mixture of N,N-dimethylacrylamide: N-(3-aminopropyl) methacrylamide hydrochloride (DMA:APMA)) for a desired amount of time. Mild agitation is applied to remove any air bubbles trapped in the nanofibers. The mixture is then illuminated with ultraviolet light. The nanofiber mesh is then flipped over and UV illumination applied to the opposite side. The coated nanofiber meshes are then rinsed with distilled water and washed overnight. The functionalized nanofibers can then be lyophilized.

Functional moieties (such as carboxy or amino groups) on the nanofibers can be measured by reversible ionic dye binding. In some aspects, it can be beneficial to provide functional group density of about 200 nmol per mg of nanofibers.

In accordance with inventive methods, polymer nanofibers are first generated by suitable techniques known in the art. Generally speaking, a number of methods have been explored to fabricate nanofibers, namely drawing, template synthesis, phase separation, self-assembly, and electrospinning. These methods are known in the art, and one of skill in the art will readily appreciate that any of them can be adapted for use in accordance with inventive principles In some aspects, nanofibers can be fabricated by electrospinning. Electrospinning is a time and cost efficient technique to produce polymer fibers and is a commonly used method to produce fiber meshes in tissue engineering. This technique is capable of producing long, continuous fibers having diameters in the range of about 3 nm to about 10 μm in diameter. The process is relatively simple and relies on the electrostatic repulsion of a polymer solution to form polymer fibers. Electrospinning generally involves the introduction of one or more polymeric materials or other fiber-forming solutions or liquid into an electric field, so that the solution or liquid produces nanofibers. A polymer solution is extruded, typically from a syringe and needle aimed at a collecting plate. Surface tension holds the polymer to the needle tip, but with the application of an electric field, a repulsive charge builds within the polymer. When a strong electrostatic field is applied to the polymer solution held in a syringe with a capillary outlet, a pendant droplet of the polymer solution from the capillary outlet is deformed into a Taylor cone. When the voltage surpasses a threshold value, the electric forces overcome the surface tension on the droplet, and a charged jet of the solution is ejected from the tip of the Taylor cone. As the jet moves toward a collecting metal screen that acts as a counterelectrode, it is split into small charged fibers or fibrils and the solvent evaporates. Thus, a nonwoven fabric mat (also sometimes referred to as a fiber mesh) is formed on the screen. Nanofibers ranging from 50 nm to 5 μm in diameter can be electrospun into a nonwoven or an aligned nanofiber mesh. Because of the small fiber diameters, electrospun textiles inherently possess a very high surface area and a small pore size. Several variables in the electrospinning procedure can be adjusted to control the fiber diameter. The main variables include the concentration of polymer dissolved in solution, polymer solution flow rate, magnitude of applied voltage and distance from the needle to the collecting plate. Additionally, fiber orientation can be directed by collecting fibers on a rotating mandrel, rather than a flat plate.

The fibrous polymer mesh formed on the collecting plate is thus composed of layers of randomly deposited, individual nanofibers. In accordance with inventive principles, the nanofiber meshes are then further processed to provide nanofiber fragments.

Optionally, the photoreactive nanofibers can be treated with UV light to crosslink the nanofibers of the mesh prior to further processing. Such crosslinking can, in some embodiments, provide additional mechanical strength of a scaffold product, as the connection between individual nanofibers can be strengthened with the crosslinking.

In one embodiment, processing of the nanofiber meshes comprises cutting the nanofiber meshes into fragments. This step of cutting can be used to produce randomly sized nanofiber fragments, or uniformly sized nanofiber fragments, as desired. Optionally, such cutting can be accomplished manually. Other processing methods include milling, grinding, homogenizing, and the like. The particular processing method employed for this step is not critical, so long as the resulting product comprises nanofiber fragments suitable for the modified heating and compression steps in accordance with inventive methods.

Various processing techniques have been developed to fabricate tissue engineering scaffolds, such as solvent casting, particulate leaching, membrane lamination, fiber bonding, phase separation/inversion, high pressure based methods, melt based technologies, microwave baking and expansion. The present inventive concepts provide a novel modified compression and heating approach that transforms nanofibrous meshes into nanofibrous scaffolds. Inventive methods have developed three-dimensional structures that achieve mechanical properties of trabecular bone from nanofibers. The resulting nanofibrous scaffolds have mechanical strength suitable for repair of soft or hard tissue within a patient's body (and in particular, repair of bone), and also provide nanotextured surface area suitable for cell attachment and proliferation. Advantageously, the nanotextured surface area can be observed on the level of the individual nanofibrous fragments that are used to prepare the scaffold, as well as the overall structure of the nanofibrous scaffold itself. The inventive scaffolds show both nanofibrillar and micro-porous features, on the level of individual nanofiber and overall scaffold levels, respectively.

The nanofibrous fragments used in accordance with inventive methods inherently possess high porosity. When electrospinning is used to generate nanofibers, the nanofiber meshes collected on the collection plate themselves possess porosity, as individual nanofibers overlap in a random orientation. This porosity is maintained when the nanofiber meshes are processed (for example, cut) to form the nanofibrous fragments. This inherent high porosity of nanofibers provides an interconnection of micropores in the overall scaffold produced.

When the nanofibrous fragments are treated with the modified compression and heating steps described herein, the fragments are bonded to each other, creating voids within the overall scaffold structure. These voids in turn provide a micro-porous scaffold structure, which allows cells within a patient's body permeate and attach to the scaffold. The micro-porous nature of the scaffold thus creates a more ECM-like environment for cell growth. One illustration of this phenomenon is osteogenesis of a bone repair site.

Control of three-dimensional pore structure within the scaffold can be of great importance for the development of scaffolds for tissue repair. The three-dimensional pore architectures promote tissue ingrowth, such as rapid penetration of cells, multicellular spheroid, nerve and blood capillary into the materials with maintenance of their biological function. If the pores employed are too small, pore occlusion by the cells can happen. This in turn can prevent cellular penetration, extracellular matrix production, and neovascularization of the inner areas of the scaffold. In accordance with inventive concepts, pore size of 100 μm or greater can be desirable due to cell size, migration requirements and transport. Relatively larger pores (for example, 300 μm or larger) can favor direct osteogenesis, since they allow vascularization and high oxygenation. At the same time, however, the upper limit of pore size and porosity can be influenced by constraints associated with mechanical properties. An increase in the void volume can result in a reduction in mechanical strength of the scaffold, which is critical for regeneration in load-bearing bones. The extent to which pore size can be increased while maintaining mechanical requirements can be dependent upon many factors, including the nature of the polymeric material and processing conditions used in its fabrication into three-dimensional scaffolds.

In some aspects, inventive methods can provide nanofibrous scaffolds having pore size in the range of about 100 μm to about 300 μm. The particular pore size can be selected depending upon the polymeric material selected to fabricate the scaffolds, as well as the tissue site to be repaired (as the latter will influence the mechanical properties desired for the scaffold).

In some aspects, nanofibrous scaffold is prepared by treating the nanofibrous fragments with a modified heating and compression process, to thereby create a three-dimensional microporous scaffold matrix having desired structural stability. Polymeric nanofibrous fragments are mixed with void forming particles such as sodium chloride (NaCl), potassium chloride (KCl), gelatin, pectin, sucrose or other sugars, and the like. The void forming particles are typically combined with the nanofibrous fragments in a solvent. The particular solvent can easily be selected using known techniques once the void-forming particles have been selected. Optionally, pore size can be further controlled by modifying the process through which void-forming particles are combined with nanofibers. For example, in some embodiments, void-forming particles can be combined with nanofibers, and the combination can be frozen. The void-forming particles can then be removed from the frozen combination, leaving behind pores of a desired size. In another embodiment, void-forming particles can be combined with the nanofibers, and the solvent can be removed by lyophilization.

The mixture is then cast into a mold, compressed and heated to a selected temperature so that the nanofibrous fragments of the casted combination bond to each other.

Compression of the nanofibrous fragments packs the fragments together, providing desirable packing density of nanofibers within the matrix, as well as pore size. Heating of the nanofibrous fragments causes adjacent fragments to bond together and is based upon the thermal transitions of a polymer. When a crystalline polymer is heated to its glass transition temperature (Tg), the translational, vibrational, and rotational energies of the molecule increase. This causes the polymer chains to become flexible and easily fold out of their packed structure. When two nanofibrous fragments are in contact, the polymer chains at the contact point can intertwine to link the particles together.

Compression can be achieved by selecting the particular force, time, and/or temperature suitable for the biodegradable polymer selected; dimensions of individual nanofibers to be utilized; final requirements for the nanofibrous scaffold (for example, soft or hard tissue application, amount of load-bearing anticipated for the tissue repair site); and the like.

Heating of the nanofibrous fragments can be accomplished using any suitable external energy source. For example, the nanofibrous fragments can be placed in an oven, microwave, or the like, to achieve the desired heating temperature. The selected temperature for the heating process can be determined based upon the polymeric material selected for nanofiber fabrication, the packing density of the nanofibrous fragments, dimensions of the nanofibers themselves, overall dimensions of the sample to be heated, desired mechanical strength of the scaffold product, target pore size of the scaffold, and the like.

Typically, heating will be performed at a temperature sufficient to cause some phase transition of the polymeric material used to fabricate the nanofibers (for example, a temperature above the Tg of the polymeric material). This phase transition allows the individual nanofibers to bond to each other, thereby increasing mechanical strength of a final nanofibrous scaffold. In some aspects, the nanofibrous fragments are heated to a temperature that will result in some phase transition of the polymeric material used to fabricate the nanofibers (and in turn to bond the nanofibrous fragments to each other), without reducing size of pores or voids between the fragments significantly. Put another way, the specific temperature range can be selected to achieve a balance between bonding the nanofibers of the nanofibrous fragments, while maintaining the pore size at a level desired for the final nanofibrous scaffold. In some embodiments, the nanofibrous fragments are heated to a temperature that is above the melting temperature of the polymer used to form the nanofibers. In other embodiments, the heating temperature can be below the melting temperature of the polymer.

Compression and heating of the nanofibrous fragments can be performed either sequentially or simultaneously. When performed sequentially, the particular order of steps is not considered critical; compression and heating can be performed in any desired order. Thus, in some embodiments, compression and heating of the nanofibrous fragments is performed simultaneously. In other embodiments, nanofibrous fragments are compressed, then heated. In still further embodiments, nanofibrous fragments are heated, and then compressed. Optionally, when heating is performed prior to compression, the nanofibrous fragments are allowed to cool partially or completely before compression. In some embodiments, it can be beneficial to compress the nanofibrous fragments while they are warm.

Fabrication of a porous scaffold suitable for hard tissue repair that matches the mechanical properties of the target tissues can be challenging. In particular, fabrication of a porous scaffold suitable for bone regeneration that matches the mechanical properties of trabecular bone (for example, compressive strength) can be challenging.

The compressed, heated material is then demolded and cooled. As the polymer is cooled (for example, to below a temperature resulting in phase change of the polymer), the energy of the molecules decreases to near zero, and the intertwined chains pack into a crystalline structure. This results in the formation of a bond between the nanofiber fragments. The degree of folding between the nanofiber fragments, which corresponds to the strength of the interfragment bond, is dependent on the cooling rate. If the polymer is allowed to cool slowly, the degree of folding will be maximized.

Optionally, void forming particles (such as salts) can then be leached from the mixture to produce a three-dimensional scaffold for tissue repair.

Three-dimensional nanofibrous scaffolds produced according to inventive methods were visualized by SEM. In some aspects, pore size was observed to be in the range of 100 to 300 µm, or 100 to 200 µm.

Cylindrical scaffolds were fabricated using a round stainless steel die, and samples were prepared having dimensions of 10 mm (length) by 7 mm (diameter). These dimensions correspond to an approximate 1.5:1 aspect ratio for compressive testing. Mechanical strength of the samples was characterized as compressive modulus using an INSTRON instrument. Stress/strain data was then used to calculate compressive modulus.

Scaffolds tested resulted in an average modulus of within the range of trabecular bone (which is typically 10 MPa to 2000 MPa). In some embodiments, scaffolds with a compressive modulus over 500 MPa, or over 1000 MPa, or over 2000 MPa, or over 3000 MPa or over 4000 MPa was obtained. In some embodiments, scaffolds with a compressive modulus in a range of about 500 MPa to about 5000 MPa, or about 500 MPa to about 4500 MPa, or about 500 MPa to about 4000 MPa, or about 500 MPa to about 3000 MPa, or about 500 MPa to about 2000 MPa, can be formed. In embodiment illustrated in the Examples, scaffold prepared in accordance with inventive principles exhibited a compressive modulus of about 4400 MPa.

In some embodiments, scaffolds fabricated in accordance with inventive principles can have sufficient strength to be useful in cortical bone replacement (bone typically having modulus of 17 MPa and compressive strength in the range of 150 to 160 MPa).

Biologically active materials, including biomolecules, small molecules, and bioactive agents can also optionally be combined with the implant to, for example, stimulate particular metabolic functions, recruit cells, or reduce inflammation. For example, nucleic acid vectors, including plasmids and viral vectors, that will be introduced into the patient's cells and cause the production of growth factors such as bone morphogenetic proteins can be included in the implant. RNAi, anti-sense RNA or other technologies can be used to reduce the production of various factors. The implant can also be seeded with cells. For example, a patient's own cells can be harvested, expanded and mixed with the implant. Alternatively, stem cells or exogenous cells can be employed. Exemplary cells for use with the invention include mesenchymal stem cells and connective tissue cells, including osteoblasts, osteoclasts, and fibroblasts.

Illustrative biologically active materials include members of the transforming growth factor β (TGF-β) family, including, but not limited to, bone morphogenetic proteins (BMPs). They play an integral role in the natural bone regeneration process because they can promote differentiation of mesenchymal stem cells (MSCs) toward an osteoblastic lineage.

Non-biologically active materials can also be optionally incorporated into the implant. For example, radiopaque, luminescent, or magnetically active particles can be included.

Biologically active and non-biologically active materials can be incorporated into the scaffold by coupling the selected material(s) via the functional moiety.

For example, when the functional moiety comprises carboxy groups, materials can be immobilized on nanofibers through an EDC/NHS coupling method. One illustrative method is described in the Examples. When the scaffold comprises aminated nanofibers, materials can be conjugated to the nanofibers through a PEG spacer. Generally, the material can be reacted with NHS-PEG3400-MAL at a molar ratio of 1:2 in PBS (pH 8.0) for a desired time at room temperature. The primary amine groups on the surface of the material are reacted with the NHS groups of the bifunctional PEG derivative. At the same time, the aminated nanofibers are thiolated using 2oiminothiolane hydrochloride (Traut's reagent, Sigma-Aldrich, St. Louis, Mo.). Then the PEGylated material can be reacted with thiolated nanofibers at a molar ratio of 1:1 in PBS (pH 7.0) for two hours at room temperature. Free material can be removed by washing with PBS-0.1% Triton X-100 overnight.

Once formed, the implantable scaffold can be placed directly into a tissue site or processed into a shape immediately prior to implantation. The term "immediately prior" is used to indicate that the desired shape is identified, the implant processed into the shape, and the shaped piece implanted into a patient as part of a surgical procedure.

Because the implant can be processed immediately prior to implantation, a surgeon does not need to know the exact size or shape of the implant site before scheduling a procedure to fill it. In addition, the surgeon does not need to schedule an additional procedure to prepare the implant site before implantation. Rather, once the characteristics of the implant site are known, the implant is processed to match it.

The implant can be formed, machined, or both, into a variety of shapes. Exemplary shapes include, without limitation, sheet, plate, particle, sphere, hemisphere strand, coiled strand, capillary network, film, fiber, disk, cone, portion of a cone, pin, screw, tube, cup, tooth, tooth root, strut, wedge, portion of wedge, cylinder, threaded cylinder, rod, hinge, rivet, anchor, spheroid, ellipsoid, oblate spheroid, prolate ellipsoid, or hyperbolic paraboloid.

Exemplary bones that can be repaired or replaced using the inventive techniques include, without limitation, ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, incus, malleus, stapes, ilium, ischium, pubic, femur, tibia, fibula, patella, calcaneus, tarsal and metatarsal bones.

In other aspect, the implant can be formed as a plate or similar support, including but not limited to an I-shape to be placed between teeth for intra-bony defects, a crescent apron for single site use, a rectangular bib for defects including both the buccal and lingual alveolar ridges, neutralization plates, spoon plates, condylar plates, clover leaf plates, compression plates, bridge plates, wave plates, and the like. Partial tubular as well as flat plates can be fabricated using the scaffolds of the invention. Alternatively, the scaffolds can be a block that is machined into a desired shape.

If desired, mechanical fasteners such as screws, rivets or sutures may be used to improve retention of the implant at the implantation site.

By using biodegradable materials, implantable scaffolds can provide a temporary site for bone regeneration and minimize or avoid problems associated with prolonged implantation.

Inventive concepts will now be described with reference to the following non-limiting Examples.

EXAMPLES

In the following Examples, morphology of all nanofibers and nanofibrous scaffolds was investigated using a Hitachi S-3500N SEM. Samples were mounted on an aluminum stub using carbon tape and gold sputter-coated before viewing.

Pore size was determined visually by scanning electron microscope (SEM) analysis. Pore size was determined as an average of a minimum of 40 pores at different points within the nanofiber or nanofibrous scaffold.

Example 1

Synthesis of Trifunctional Triazine Crosslinker

A triazine crosslinker was synthesized as follows. 1.2 g (4 mmol) of triglycidyl isocyanurate (Aldrich Chemicals, Milwaukee, Wis.) and 2.4 g (12 mmol) of 4-hydroxybenzophenone (Aldrich Chemicals, Milwaukee, Wis.) were mixed in a 50-ml round bottom flask containing a magnetic stir bar. The flask was flushed with argon for 10 min and heated to 130° C. in an oil bath. Once the reaction mixture melted, 6 mg (0.02 mmol) of triphenylphosphine (Aldrich Chemicals, Milwaukee, Wis.) was added. The mixture was stirred for another 2 minutes under argon and cooled to room temperature. The reaction residue was dissolved in 30 ml chloroform, then washed with 4N NaOH (30 ml×3) and deionized water (30 ml×3). The organic layer was dried over magnesium sulfate and concentrated to dryness under reduced pressure. The product was purified by column chromatography (silica gel, 230-400 mesh, Whatman, Inc.) using ethyl acetate as eluent ($R_f$~4.5). The fractions containing the pure product were combined and concentrated under reduced pressure and a white powder was obtained after drying under vacuum (yield 70%).

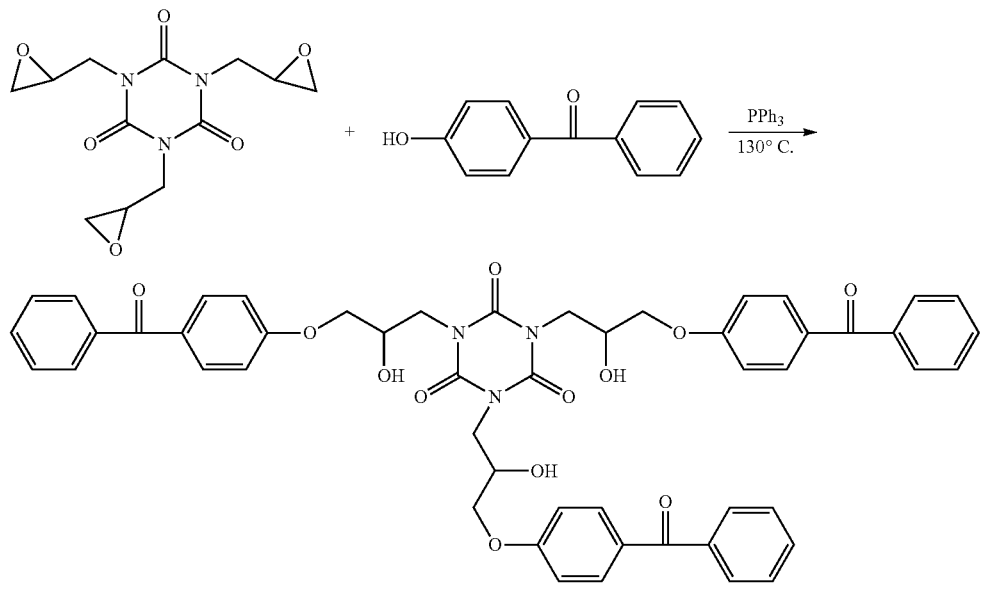

$^1$H NMR (CDCl$_3$) confirmed the structure of the product. The peaks at d 7.78 ppm (m, 12H), 7.46 ppm (m, 9H), 6.98 ppm (m, 6H) were the typical signals from 4-substituted benzophenone. The peak at d 4.35 ppm (m, 6H) was assigned to the protons of methylene connected to phenoxy group. The peak at d 4.13 ppm (m, 9H) was a combination of 6 protons of 3 methylene groups connected to nitrogen atom and 3 protons from 3 methine groups. The peak at d 3.00 ppm (s, 3H) corresponded to hydroxyl groups.

Example 2

Preparation of Photoreactive Nanofibers

Photoreactive nanofibers were prepared by combining the crosslinker prepared as described in Example 1 with a biodegradable, synthetic polymer, followed by electrospinning the combination to form nanofiber meshes. Further, two different synthetic polymer solutions were simultaneously electrospun into one nanofiber mesh.

Photoreactive polycaprolactone nanofiber meshes were prepared by electrospinning of PCL solutions containing selected amounts of a photoreactive crosslinker as follows. The triazine crosslinker prepared in Example 1 was combined with 50:50 DMF/THF solvent to provide a 10% (w/w) crosslinker solution. The crosslinker solution was then combined with 5 ml 0.14 g/ml poly(ε-caprolactone) (PCL, Mw=80,000) and loaded into a 5 ml syringe (Norm-Jact, Henke Sass Wolf GMBH). After removal of air bubbles, a 27 G blunt needle 1.5 inch (SAI, B27-150) was attached to the syringe.

A separate 1 ml tuberculin syringe (Norm-Jact, Henke Sass Wolf GMBH) was filled with 1 ml 0.14 g/ml PCL (Mw=80,000) with 1% (w/w) triazine crosslinker (prepared as described in Example 1) in 50:50 DMF/THF solvent mixture. After removal of air bubbles, a 27 G blunt needle 1.5 inch (SAI, B27-150) was attached.

Both needles were clamped together to a high voltage power supply (Gamma High Voltage Research, USA). Both syringes were placed on the same slot of the syringe pump (KD Scientific, USA) and locked in place. The feed rate of the syringe pump was fixed at 0.3 ml/hour. Nanofibers were fabricated by electrospinning at 14 kV. The nanofibers were collected as meshes onto grounded aluminum foil located at a fixed distance of 15 cm from the needle tip.

The nanofiber meshes were then removed, placed in a vacuum chamber for at least 48 hours to remove organic solvent residue, and then stored in a desiccator. The dried nanofibers were visualized using scanning electron microscopy (SEM). Diameter of the nanofibers was 200 to 300 nm. Pore size was 1-10 μm.

The nanofibers were then functionalized with polymers containing reactive groups as follows. Polymers containing carboxyl (PAA) or amino groups (PEI) were covalently bound to nanofiber surface through the well-established benzophenone photochemistry. For deposition, a certain amount of nanofiber mesh was immersed in 20 ml of 50 mg/ml PAA or PEI aqueous solution for 30 minutes in a quartz round dish (Quartz Scientific, Inc., Fairport Harbor, Ohio). Mild agitation was applied to remove the air bubbles trapped in the nanofibers. Two minutes of UV irradiation was then applied to the mixture using a UVM400 ultraviolet lamp (Harland Medical, Eden Prairie, Minn., distance from light source was 8 inches). The nanofiber mesh was flipped over and UV illumination applied again. The coated nanofiber meshes were rinsed with distilled H$_2$O 3 times and washed overnight. The functionalized nanofibers were then lyophilized.

The amount of functional groups (carboxy and amino) on the nanofibers was measured by reversible ionic dye binding. Calibrations were done with the respective dyes in the solvents used for elution. The fluorescent/UV/vis measurements were performed on a SpectraMax M2 Multi-detection Reader from Molecular Devices, Inc.

For quantitation of carboxy groups, nanofiber samples were shaken overnight in 10 ml of 10 mg/l thionin (Aldrich Chemicals) in ethanol at room temperature, rinsed three times with ethanol for 30 seconds and then immersed in 10 ml of a solution of 0.01 N HCl in a 1:1 mixture of ethanol and water. After shaking for 1.5 h, fluorescence of the solution was recorded at 620 nm (excitation 485 nm).

For quantitation of amine groups, nanofiber samples were shaken overnight in a solution of 50 mmol/L Orange II (Aldrich Chemicals) in $H_2O$ (pH 3, HCl) at room temp. The samples were washed 3 times with $H_2O$ (pH 3) and immersed in 10 ml of $H_2O$ (pH 12, NaOH). After shaking for 15 minutes, the UV/Vis absorption of the solution was recorded at 479 nm.

The functional groups on the nanofiber surface were determined based on 1:1 complexation between functional groups and dye molecules. Results indicated functional group density in the range of 10-500 nmol carboxy groups per mg of nanofibers, and in the range of 1-100 nmol amine groups per mg of nanofibers, respectively.

Electrospun nanofiber meshes were cut into 1×1 cm square shapes and both sides of the mat were sterilized by UV irradiation in a laminar flow hood for 1 hour. Biocompatibility of functionalized nanofibers was assessed by with human calvariae osteoblasts (HCO) using the WST-1 dye reduction assay. Results (not shown) indicated the functionalized nanofiber meshes were biocompatible with osteoblasts.

The porosity of the nanofiber meshes was determined by a liquid displacement method. 40-50 mg of nanofiber was immersed in a graduated cylinder containing $V_1$ volume of isopropanol (IPA). A bath sonication was applied to force IPA to enter the pores and eliminate air bubbles. After 10 minutes, the volume was recorded as $V_2$. The wetted sample was removed from the cylinder and the residual IPA volume was measured as $V_3$. The porosity of the nanofiber mesh was calculated as:

$$\text{Porosity} = (V_1 - V_3)/(V_2 - V_3)$$

Where $(V_1-V_3)$ is the volume of IPA held in the nanofibers, which represents the volume of porous space in the nanofibers. $(V_2-V_3)$ is the total volume of nanofibers and porous space. Results indicated the nanofiber meshes had porosity of 70%-90%.

Example 3

Preparation of Nanofibrous Scaffolds

The photoreactive nanofibers prepared in Example 3 were processed using a modified heating and compression treatment, to thereby produce nanofibrous scaffolds.

After air dry, the nanofiber meshes prepared in Example 2 were cut into small strips with scissors to sizes suitable for placement in a tissue homogenizer and further homogenized in a conical tube with IPA. An ice bath was used to prevent overheating of the mixture during homogenization. The nanofibrous fragments were collected by centrifugation at 1500 rpm and gravity filtration through a Buchner funnel. The resulting nanofibrous fragments consisted of a white powder and had an average dimension of 1×1 mm. See FIG. 1.

Next, 700 mg of the nanofibrous fragments were suspended in 70:30 DI water: 27 wt % NaCl solution and lyophilized for two (2) days. The nanofibrous fragments were then filled into a round stainless steel die with a diameter of 13.5 mm, and compressed at room temperature for two. (2) minutes under 1,200 lbs force. The temperature during compression was above the $T_g$ and below the melting temperature for PCL.

The compressed sample was then demolded and placed into an oven, where it was heated at 100° C. for 1 hour. The resulting cylindrical sample was removed from the oven and soaked in DI water overnight to remove salts, followed by an IPA rinse for 1 hour. The nanofibrous scaffold was vacuum dried overnight.

Figure 2:
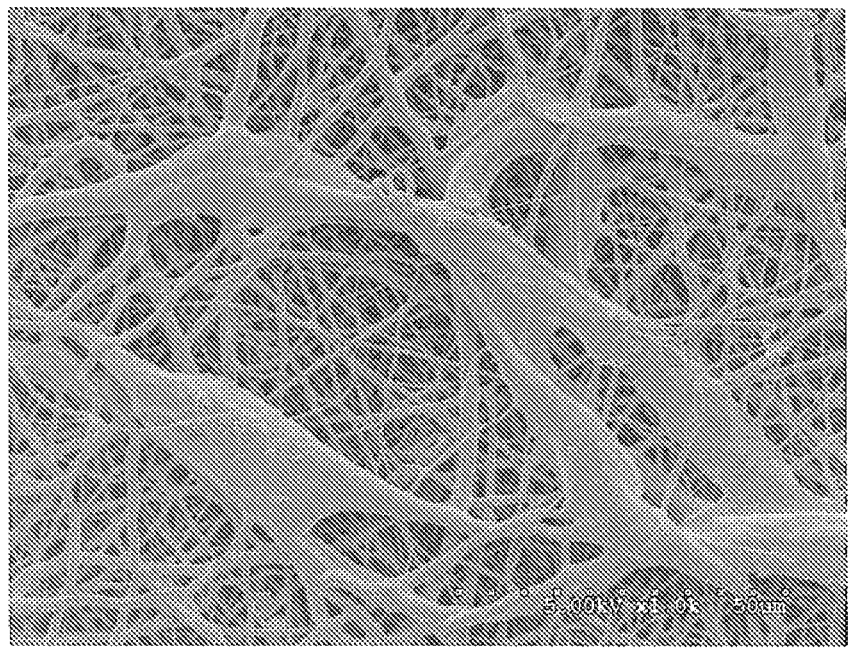
FIG. 2 shows an SEM image of nanofiber meshes produced in accordance with inventive principles.
Figure 3A:
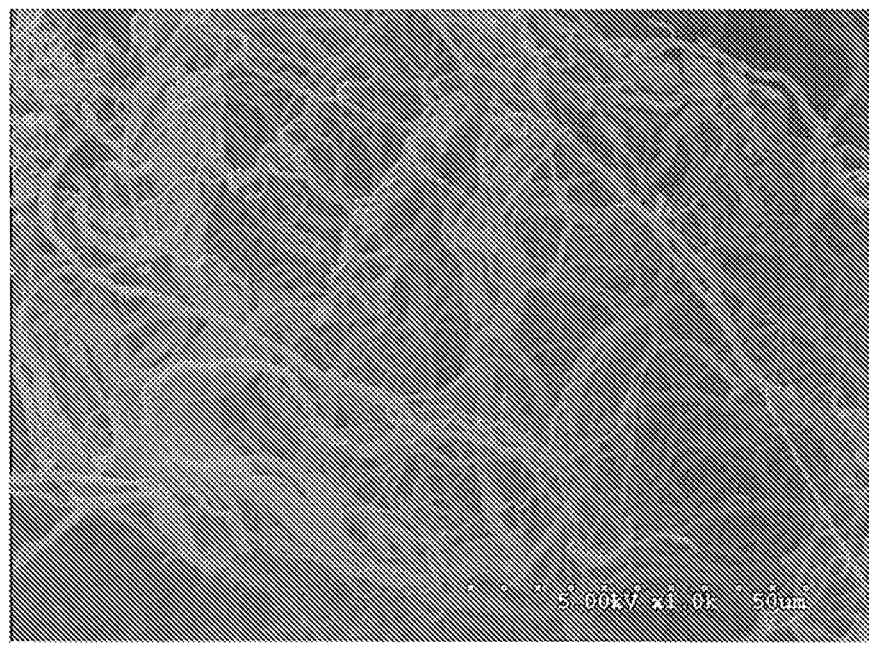
FIG. 3 shows SEM images of a highly porous three dimensional nanofibrous scaffold in accordance with inventive principles.
Figure 3B:
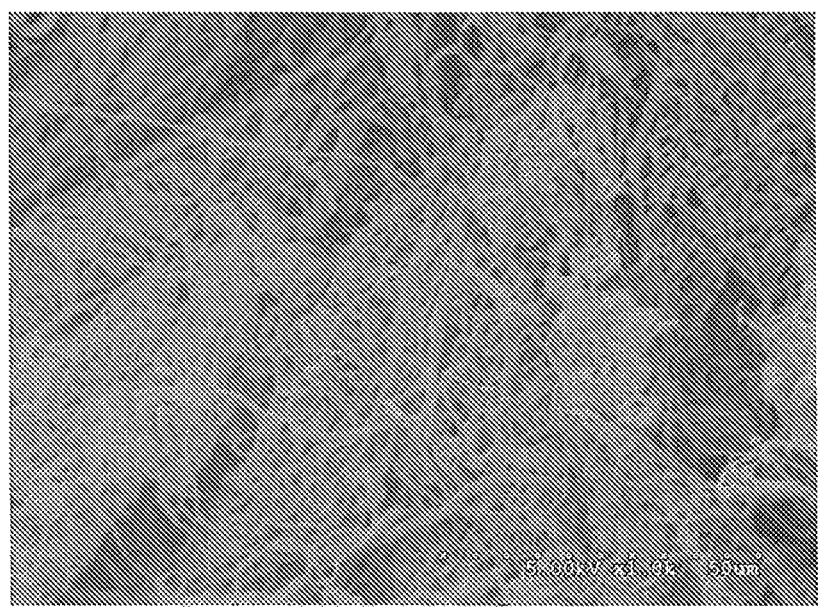
Figure 4:
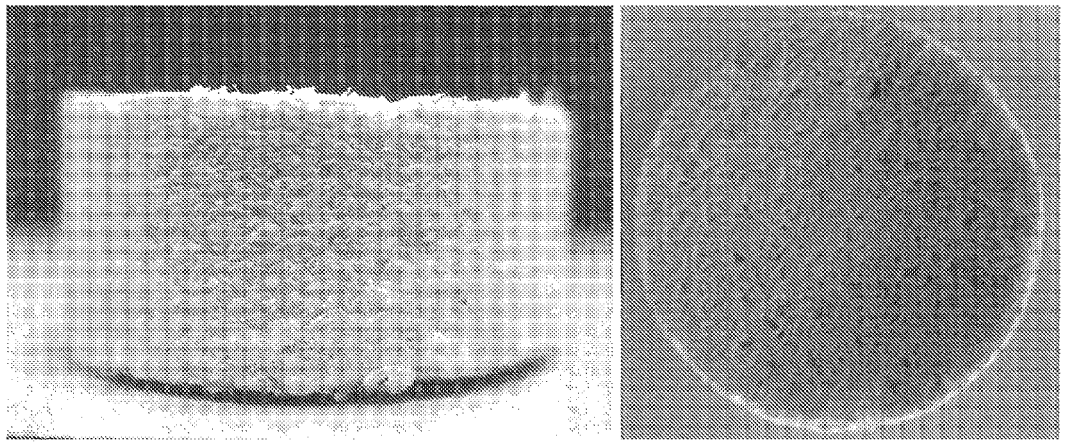
FIG. 4 shows nanofibrous scaffold prepared in accordance with inventive principles.
Figure 5:
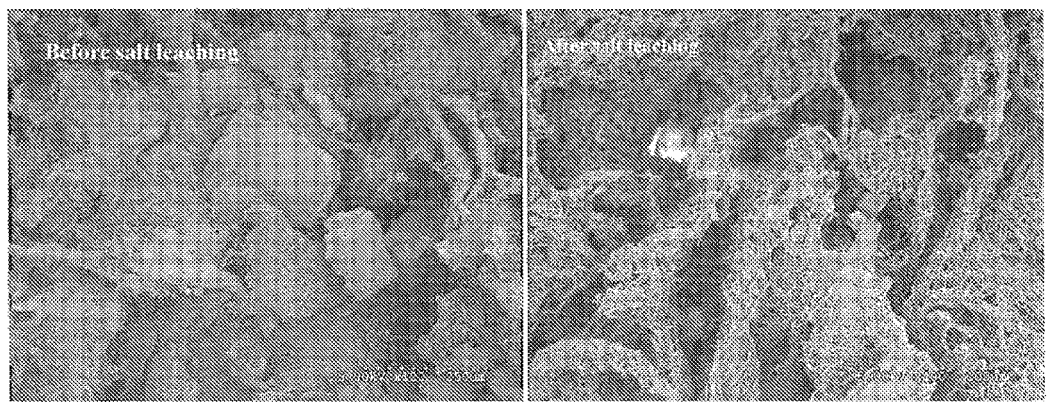
FIG. 5 shows SEM images of nanofibrous scaffold before and after removal of void-forming particles.

The modified compression and heating method produced nanofibrous scaffolds with a diameter of 7 mm and thickness of 10-20 mm. Scaffolds were observed by SEM. Cylindrical samples were cut into sections (1 mm thickness) which were affixed to an SEM stage. Images of scaffold prepared in accordance with inventive principles are illustrated in the figures. FIG. 2 shows an SEM image of an embodiment of the invention, where co-electrospun nanofibers were visualized. The image shows that the nanofibers containing 1% crosslinker melted and bonded the nanofibers mesh together; the intact individual fibers with small diameter were the nanofibers containing 10% crosslinker. FIG. 3 shows SEM images of three-dimensional nanofibrous scaffolds produced in accordance with inventive concepts. The SEM images illustrate a highly porous three-dimensional structure with nanofibrous texture. The nanofibrous scaffolds thus exhibit nanotexture from the nanofibers, and a micro-porous structure resulting from voids created in the scaffold. FIG. 4 illustrates three-dimensional nanofibrous scaffolds prepared as described herein. FIG. 5 illustrates SEM images of the nanofibrous and micro-porous structure of inventive nanofibrous scaffolds.

Porosity of the nanofibrous scaffolds was determined by the liquid displacement method described above in Example 2. Porosity measured by the liquid displacement method was 40%-70%.

Pore size within the nanofibrous scaffold was 100 to 200 μm. Pore size was determined by SEM as an average of a minimum of 40 pores at different points within the nanofibrous scaffold.

Mechanical properties of the nanofibrous scaffolds were measured by compressive testing using cylindrical scaffolds (10 mm in length and 7 mm in diameter). Compressive testing was conducted using an Instron mechanical testing machine (Instron-Sacks Planar Biaxial Soft Tissue Testing System or Instron Model 4204), and data were analyzed using the software accompanying the machine, which automatically calculated compressive modulus from stress/strain data. Compression was applied with a crosshead speed of 5 mm/minute at ambient temperature and humidity. No difference was observed in the stress-strain curves between unmodified, acid functionalized and protein conjugated scaffolds. Maximum compressive modulus was 4400 MPa.

Example 4

Differentiation of BMSC on BMP-2 Conjugated Nanofibrous Scaffolds

Scaffolds were seeded with bone marrow stromal cells (BMSCs) to observe the ability of the nanofibrous scaffolds to support growth and differentiation of these cells. Human bone marrow stromal cells were purchased from Lonza Group Ltd. (Switzerland). The cells were cultured at 37° C. in a humidified atmosphere of 5% $CO_2$ in low-glucose Dulbeccomodified Eagle's Medium (DMEM) (Gibco BRL; Life Technologies, Gaithersburg, Md.) supplemented with 10% fetal bovine serum (FBS), penicillin (100 U/mL), streptomycin (100 μg/mL) and Fungizone (0.25 μg/mL).

Prior to cell seeding, BMP-2 conjugated scaffolds were prepared by activating 7×7×3 mm PAA functionalized nanofibrous scaffold (prepared as described above) with 500 μl 10 mg/ml EDC and 5 mg/ml NHS for 2 hours, rinsing with pH 4.5 cold water, finally reacting with 300 μl 16.67 μg/ml BMP-2 in PBS 7.4 at 4° C. overnight. The BMP-2 conjugated scaffolds were rinsed with sterile water three times and sterilized by UV irradiation for 30 seconds per side using a Harland Medical UV system, and pre-wetted for 24 hours in Hanks' Balanced Salt Solution (HBSS; BioSource International, Camarillo, Calif.).

Pre-processed scaffolds were then placed in 24-well tissue culture plates (Corning Glass Works, Corning, N.Y.). Cell suspension was seeded into the scaffolds in 300 μL volume using an 18 gauge needle. Equal numbers of cells were seeded onto BMP-2 functionalized and control nanofibrous scaffolds. Control scaffolds were acid functionalized without BMP-2 conjugation. Soluble BMP-2 (500 ng) was added to control scaffolds. Cells attached and spread on BMP-2 conjugated nanofibrous scaffolds and there was no need to co-immobilize cell adhesion peptides. Calcein staining showed MSC cells successfully attached to BMP-2 conjugated nanofibrous scaffolds (data not shown here).

What is claimed is:

1. A method of producing an implantable nanofibrous scaffold having mechanical stability of bone, the method comprising steps of:
   (a) generating biodegradable, synthetic nanofibers from a biodegradable, synthetic polymer having a Tg and a melting temperature;
   (b) processing the nanofibers to generate nanofiber fragments;
   (c) combining void forming particles with the nanofiber fragments to form a nanofiber fragment/particle combination;
   (d) compressing the nanofiber fragment/particle combination at a temperature between the Tg and the melting temperature of the biodegradable, synthetic polymer; and
   (e) heating the nanofiber fragment/particle combination at a temperature above the Tg of the biodegradable, synthetic polymer to generate a porous nanofibrous scaffold, wherein the compressing and heating steps transform the nanofiber fragments into implantable nanofibrous scaffolds having mechanical stability of bone comprising a compressive modulus in the range of 500 to 5000 MPa.

2. The method according to claim 1 wherein the nanofibers of step (a) comprise photoreactive nanofibers.

3. The method according to claim 2 wherein the step (a) comprises generating polycaprolactone photoreactive nanofibers.

4. The method according to claim 1 wherein the step (a) comprises electrospinning.

5. The method according to claim 1 further comprising a step of providing a functional moiety to the nanofibers.

6. The method according to claim 5 wherein the functional moiety comprises an acid or amine functional group.

7. The method according to claim 2 further comprising a step of illuminating the nanofibers of step (a).

8. The method according to claim 1 wherein the step (b) comprises cutting the nanofibers to generate nanofiber fragments.

9. The method according to claim 1 wherein steps (d) and (e) are performed simultaneously.

10. The method according to claim 1 wherein step (e) is performed after step (d).

11. The method according to claim 1 wherein the void forming particles are selected from the group of sodium chloride, potassium chloride, gelatin, pectin, sucrose or other sugars, or a combination of any two or more of these.

12. The method according to claim 11 further comprising a step (f) removing the void forming particles from the porous scaffold.

13. The method according to claim 6 further comprising a step of coupling a biomolecule or bioactive agent to the nanofibers via the functional moiety.

14. The method according to claim 13 wherein the biomolecule is an osteogenic protein.

15. The method according to claim 14 wherein the osteogenic protein is bone morphogenic protein or one or more ECM proteins.

16. The method according to claim 1 wherein the compressing and heating steps transform the nanofiber fragments into nanofiber scaffolds having mechanical stability of bone comprising a compressive modulus in the range of 2000 to 5000 MPa.

17. The method according to claim 1 wherein the compressing and heating steps transform the nanofiber fragments into nanofiber scaffolds having mechanical stability of bone and a porosity in a range of 30% to 40%.

18. The method according to claim 1 wherein the compressing and heating steps transform the nanofiber fragments into nanofiber scaffolds having mechanical stability of bone and an average pore size that is greater than 100 μm.

19. The method according to claim 1 further comprising a step of crosslinking the nanofibers prior to step (b).

* * * * *